United States Patent [19]
Diedrich et al.

[11] Patent Number: 4,760,135
[45] Date of Patent: Jul. 26, 1988

[54] PHLORETIN AND PHLORIZIN DERIVATIVE CONTAINING COMPOUNDS

[75] Inventors: Donald F. Diedrich; Susanne L. Diedrich, both of Lexington, Ky.

[73] Assignee: University of Kentucky Research Foundation, Lexington, Ky.

[21] Appl. No.: 647,996

[22] Filed: Sep. 6, 1984

[51] Int. Cl.$^4$ ............................................ C07H 15/04
[52] U.S. Cl. .................................... 536/17.9; 536/4.1; 536/17.2; 536/51; 536/52; 536/56; 536/112; 536/114
[58] Field of Search .................... 536/52, 114, 56, 51, 536/112, 4.1, 17.2, 17.9; 514/54, 59, 60

[56] References Cited

U.S. PATENT DOCUMENTS 3,523,937  8/1970  Biegeleisen ........................ 536/18.4
4,224,439  9/1980  Ayers et al. .

OTHER PUBLICATIONS

Takeshi Kasagi, "Inhibition of Glucose Transport in the Rat's Small Intestine by Cellulose-Phlorizin", 1981, p. 250.

Diedrich, "The Comparative Effects of Some Phlorizin Analogs on the Renal Reabsorption of Glucose", 1962, pp. 688–700.

Diedrich, "In Vitro Evaluation of Relative Inhibitory Potency of Phlorizin and Its Congeners", 1965, pp. 621–626.

Diedrich, "Competitive Inhibition of Intestinal Glucose Transport by Phlorizin Analogs", 1966, pp. 248–246.

Bode, Baumann & Diedrich, "Inhibition of [$^3$H] Phlorizin Binding to Isolated Kidney Brush Border Membranes . . . ", 1972, pp. 134–149.

Vick, Diedrich & Baumann, "Re-evaluation of Renal Tubular Glucose Transport Inhibition by Phlorizin Analogs", 1973, pp. 552–557.

Warden, (Dissertation), "Intestinal Absorption of Glucose Hydrolyzed . . . Membranes", 1982, pp. 188+.

Primary Examiner—J. R. Brown
Assistant Examiner—Elli Peselev
Attorney, Agent, or Firm—King and Schickli

[57] ABSTRACT

Compounds including phloretin and/or phlorizin derivatives coupled to an undigestible and non-absorbable matrix are provided. The compounds have pharmacological efficacies. They inhibit sugar uptake from the intestine and may be used in composition form in methods for treating diabetes and for promoting weight loss. A method for the manufacture of these compounds and a novel intermediate phlorizin derivative for making these compounds are also disclosed.

15 Claims, 1 Drawing Sheet

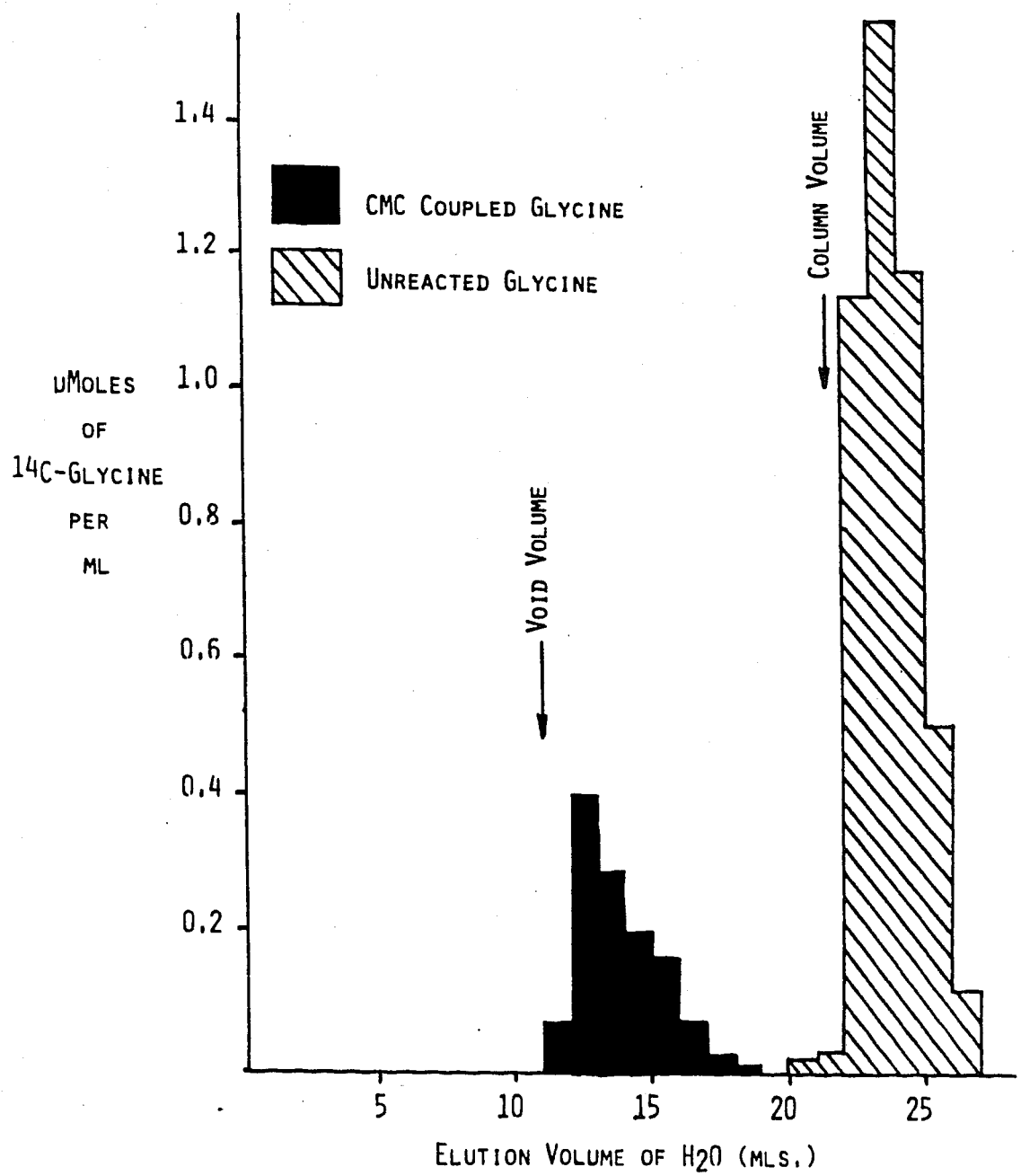

PHLORETIN AND PHLORIZIN DERIVATIVE CONTAINING COMPOUNDS

TECHNICAL FIELD

The present invention relates to innovative compounds having phloretin or phlorizin moieties and their use as a new and novel class of clinically safe pharmacological agents. More particularly, the present invention relates to certain new phloretin and phlorizin derivative containing compounds, pharmaceutical compositions thereof, their methods of preparation, and their methods of use in inhibiting sugar uptake from the small intestine for the treatment of diabetes, obesity and dumping syndrome.

BACKGROUND ART

Current pharmacological therapy for the overweight patient focuses on two approaches: appetite regulation and modulation of intestinal absorption processes. The first approach involves the administration of anoretic agents, such as amphetamines, to the patient in order to control caloric intake. Typically, the amphetamines are used as short term adjuncts to a nutritionally and/or behaviorally designed weight reduction program. While these agents are strong suppressors of appetite, their systemic action is associated with dangerous central nervous system side effects and humoral/neurotransmitter imbalances.

The second approach to control body weight involves the reduction of the availability of nutrients by affecting digestion and/or absorption. The success of intestinal by-pass operations for the treatment of obesity has encouraged the search for oral agents which might produce a chemically induced, reversible form of altered intestinal absorption. A number of compounds have been examined in studies designed to block the intestinal uptake of lipids. Such an approach, however, disadvantageously causes essential lipid-soluble vitamin malabsorption and other serious disorders (Dobbins, W. O., Herrero, B. A. and Mansbach, C. M., Am. J. Med. Sci. 255 (1968) 63; Bray, G. A., "Drug Therapy for the Obese Patient" in *The Obese Patient*, (1976) p. 353, Saunders, Philadelphia; and Evans, E., Miller, D. S., Samuel, P. D. and Burland, W. L., Postgrad. Med. J. 51, Suppl. 1 (1975) 1204).

In order to avoid this problem, recent research has been directed toward the development of "starch blockers". An example of these is a preparation of amylase inhibitors which are proposed to block carbohydrate absorption (Keup, V. and Puls, W., Arch. Pharmacol. 297 Suppl. (1975) R85). The rationale for this approach relies on the fact that the enzyme amylase, normally secreted in saliva and from the pancreas, hydrolyzes starch randomly to glucose and maltose. The maltose is then degraded by maltase to the mono-saccharide glucose. The monosaccharides are the only form of any dietary carbohydrate that is absorbed by intestinal transport mechanisms. Thus, if the amylase is inhibited from hydrolyzing the starch, intestinal absorption is blocked. Over 100 different varieties of these "starch blocker" preparations have been placed on the market. They are widely sold by pharmacies and health food stores. The use of these "over-the-counter" offerings has been so attractive that over a million tablets were consumed daily in the United States during the first part of 1982. These consumption figures indicate that the public is remarkably responsive to claims for diet and food supplements promising a short cut to weight control without dietary discipline. Despite the commercial success of these starch blockers, however, there is no evidence that these preparations actually inhibit starch or calorie absorption in vivo. In fact, in a decisive study with human volunteers, Fordran and his coworkers showed no increase in calories lost in feces caused by these amylase inhibitors (Bo-Linn, G. W., Santa Ava, C. A., Morawski, S. G. and Fordran, J. S., New Engl. J. Med. 307 (1982) 1413).

It is generally accepted that the transport system responsible for the active renal reabsorption of D-glucose is localized in the luminal membrane or brush border of proximal tubular cells (see Vick, Diedrich and Baumann, Am. J. of Physiol., Vol. 224, No. 3, March (1973) 552–557). Experimental evidence indicates that the glucose interacts with a component or carrier of the membrane that facilitates the entry of the sugar into the cells. For example, the final step in carbohydrate assimiliation by the small intestine has been shown to be the active absorption of enzyme generated mono-saccharides via a $Na^+$-dependent transporter in the epithelial brush border membranes.

Phlorizin is known to be a highly effective and specific blocker of sugar absorption from the intestinal tract. In fact, studies have indicated that this naturally occurring compound found in the bark and other components of apple and other fruit trees is a potent competitive inhibitor of the sugar transport process having an affinity for the sugar transporter of about 1,000 times greater than D-glucose (Bode, F., Baumann, K., and Diedrich, D. F., Biochem. Biophys. Acta 290 (1972) 134). Phlorizin, however, is not a clinically useful and safe pharmacological agent that may be used in the management of diabetic and obese patients.

Orally administered phlorizin not only blocks the in vivo intestinal absorption of glucose in rats and dogs but it also causes a "phlorizin diabetes" or glucosuria. Some of the phlorizin survives the hydrolytic environment of the gastrointestinal tract, is absorbed intact, and is carried to the kidneys where it blocks the sugar transporter. Furthermore, as some of the phlorizin travels through the digestive system, it is hydrolyzed by the intestinal epithelia to phloretin (Diedrich, D. F., Arch. Biochem. Biophys, 127 (1968) 803) which readily enters the blood stream to cause at appropriate levels profound toxic effects at all sites in the body.

While phlorizin is not a clinically useful and safe pharmacological agent, it is a valuable study tool. Tests and studies of phlorizin have shown that the glucose moiety of phlorizin is an essential substituent of a potent sugar uptake inhibitor molecule. Experimental results bear out this postulate with regard to at least a part of this moiety (Diedrich, D. F., "In vitro Evaluation of Relative Inhibitory Potency of Phlorizin and its Congeners", Am. J. Physiol., Vol. 209, No. 3, September (1965)). Clearly, however, since the affinity for the transport site by phlorizin is approximately 1,000 times greater than that shown by glucose, some feature of the aglucone moiety of phlorizin facilitates the interaction of the glucosidic portion of the molecule with the receptor. As a result of the interaction, the stability of the phlorizin formed complex is much greater than that formed with the free sugar.

Further experiments with phlorizin and other structurally related glycosides have resulted in the identification of several features which describe the critical structure of a potent inhibitor of the absorption of glucose. The inhibitory agent is one that possesses atomic groupings in a specific three-dimensional pattern. The pattern favors an association with the membrane receptor. The molecule is visualized to be bound at two or more loci. A primary bond is formed through the interaction of the glycosidic moiety with appropriate groups of the membrane constituent. The linkage presumably is formed through hydrogen bonds that involve at least the hydroxyl groups on C-3 and C-4 of the sugar group. The most stable primary interaction occurs when these hydroxyl groups are situated in the more chemically reactive equatorial position. A secondary bonding of the aglucone portion of the inhibitor molecule to a locus on the biological surface is adjacent to, but removed from the plane of the glucose transporting site. The linkage is probably through hydrogen bonding between the oxygen of the 4-hydroxyphenyl moiety and a membrane constituent capable of serving as a hydrogen donor at physiological pH. The locus is approximately 13–16 Å removed from the transport site to which glucose is normally bound.

The present invention uses the information gained from the studies of the geometric configuration and chemical structure of the inhibitory mechanism of phlorizin, phloretin and related derivatives and advances the art by providing compounds and compositions having pharmacological efficacies. Particularly the compounds act as pharmacological agents that are clinically useful and safe in inhibiting sugar uptake without systemic side effects.

SUMMARY OF THE INVENTION

Accordingly, it is a primary object of the present invention to provide innovative and novel compounds having phloretin or phlorizin moieties and pharmacological efficacies. A method for the manufacture of these compounds is also provided.

A further object of the invention is to provide certain phloretin and phlorizin derivative containing compounds that act as specific inhibitors of glucose absorption from the intestine.

An additional object of the present invention is to provide new phloretin and phlorizin derivative containing compounds that are clinically safe and useful to selectively inhibit glucose absorption from the intestine.

A still further object of the invention is to provide certain phloretin and phlorizin derivative containing compounds and methods for their use in the management and treatment of sugar transport disorders.

Another object of the present invention is to provide novel phloretin and phlorizin derivative containing compounds and pharmaceutical compositions for inhibiting sugar absorption from the intestinal tract.

A still further object of the invention is to provide phloretin and phlorizin derivative containing compounds, pharmaceutical compositions and methods for their use in the treatment of diabetes, obesity and dumping syndrome.

Other objects and advantages of the present invention will become apparent as the description thereof proceeds.

In satisfaction of the foregoing objects and advantages, there is provided by this invention compounds of pharmacological efficacy including phloretin and/or phlorizin moieties formed from an intermediate derivative selected from those of the following formulae:

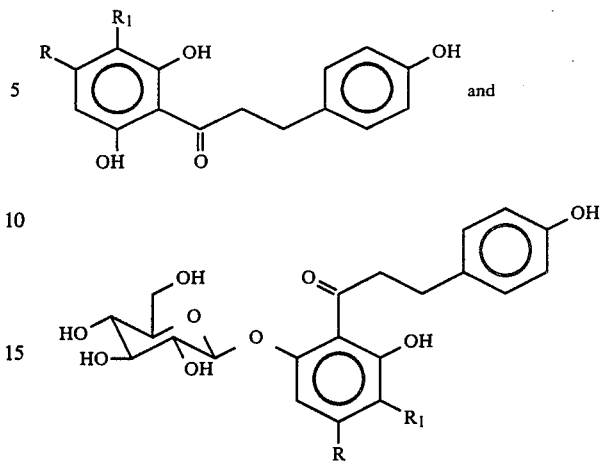

wherein R is —OH or —H and $R_1$ is a primary amine moiety. Specific examples of intermediate compounds used to form the complete compound of the invention include 4'-deoxyphlorizin-5'-benzylamine, phlorizin-5'-benzylamine and phloretin-3'-benzylamine.

In accordance with the objects and advantages of the present invention, compounds for inhibiting sugar uptake from the small intestine comprise a reaction product formed from serially coupling (1) an undigestible and non-absorbable matrix with a leash forming compound to form a first intermediate product; (2) the first intermediate product with an intermediate phloretin or phlorizin derivative (as defined above) to form a second intermediate product; and (3) the second intermediate product with a promoter forming compound that enhances the affinity of the resulting sugar uptake inhibitory compound of the invention for the surface membrane of the small intestine.

The matrix is a polysaccharide with monomeric units ranging from 150–500. The individual monomers may include glucose, mannose, galactose or any mixtures of these. The monomers may also carry appropriate functional groups on either the free primary hydroxyl or the free secondary hydroxyls. Functional groups include carboxymethyl (—O—$CH_2$—$CO_2H$), 2-hydroxy-3-bromopropyl (—O—$CH_2$—CHOH—$CH_2Br$), aminopropyl-diethoxysilane (—Si(O$C_2H_5$)$_2$—$C_3H_6NH_2$), amine (—$NH_2$), and amide (—NH—CO—$CH_3$). Preferably, the matrix is of high molecular weight of from 25,000 to 90,000 daltons with even higher values possible. Specific examples of matrices include carboxymethylcellulose; sodium carboxymethylcellulose; a carboxymethyl derivative of a galactomannan from the guar plant (available as Jaguar CMG; from Celanese Corporation); a dextran, such as BHP-activated Dextran 70 (available from Pharmacia Fine Chemicals, Uppsula, Sweden); CH-Sepharose (available from Pharmacia Fine Chemicals); and a N-hydroxysuccinimide-activated ester of a derivatized cross-linked agarose gel bead support, such as Affigel 15 (available from Biorad Laboratories).

The leash forming compounds are coupled via amide linkages with the functional groups of the matrix. The leashes or spacer arms formed serve to hold the later coupled inhibitory phloretin or phlorizin derivatives away from the backbone of the matrix for reaction with the sugar transporter of the intestinal membrane. For example, the leash forming compounds couple to 0-100% of the carboxy groups of a sodium carboxymethylcellulose matrix. Specific leash forming compounds include glycine; N,N-diaminopropylmethylamine; tartaric acid; glutardialdehyde; and amino acids with the formula $NH_2-(CHOH)_n-CO_2H$, wherein $n=1-6$.

The intermediate phloretin or phlorizin derivative is then coupled to the first intermediate product formed by coupling the leash forming compound with the matrix. The coupling is through the amine moiety of the 5' C of a phlorizin intermediate compound or the 3' C of a phloretin intermediate compound. The amine moieties bind remaining unbound functional groups of the matrix and the distal ends of the leash forming compounds via amide linkages that are resistant to the proteolytic enzymes of the digestive tract.

The resulting second intermediate product is then coupled with a promoter forming compound. Promoter forming compounds include ethylenediamine and ethanolamine. The promoter forming compound couples to any remaining free functional groups of the matrix following coupling of the matrix, leash forming compound and intermediate phloretin or phlorizin derivatives.

In an additional aspect of the present invention, in accordance with its objects and purposes, sugar uptake inhibiting compositions are provided having as the active ingredient compounds as set forth above. Methods are also provided for using these compositions in treating diabetes and dumping syndrome, as well as in promoting weight loss. Each of these methods involves the administration to the patient of an effective dosage of the sugar uptake inhibitory compounds of the invention.

The effective dosage is administered in the form of a pharmaceutical preparation or composition wherein the inhibitory compound is admixed with a pharmaceutical organic or inorganic excipient. Suitable excipients are substances that do not react with the novel inhibitory compounds. Specific examples of such excipients include water, gum and starch. Of course, other known medicinal excipients may be used. The compositions may be designed to be taken orally in tablet or capsule form. Preferably, the compositions are administered in an enteric-coated form to protect the amide linkages connecting the various ligands with the non-digestible matrix from the acidic environment of the stomach.

In another aspect of the invention, in accordance with its objects and purposes, a method for the preparation of compounds effective in inhibiting sugar uptake in the small intestine without harmful side effects is provided. The method involves the steps of: (1) coupling a leash forming compound with an undigestible and non-absorbable matrix to obtain a first intermediate product; (2) coupling the first intermediate product with an intermediate phloretin or phlorizin derivative to obtain a second intermediate product; and (3) coupling the second intermediate product with a promoter forming compound.

The initial coupling step includes the steps of mixing the leash forming compound and matrix together in solution and adding a catalyst to promote the coupling and the formation of the first intermediate product. During the reaction, the pH of the solution is maintained at substantially 5.8. The resulting first intermediate product is then purified by dialyzing.

The second coupling step includes the steps of dissolving the first intermediate product, for example, a glycine-carboxymethylcellulose matrix, in water and the intermediate phloretin or phlorizin derivative in ethanol. The solutions are then mixed together and brought to a pH of substantially 5.8 with the ethanol level of the mixed solutions being approximately 15%. Following the adding of a catalyst to promote the formation of the second intermediate product, the pH and ethanol concentration are maintained at these levels. The resulting second intermediate product is then purified by chromatography.

The third coupling step includes the steps of forming a solution of the second intermediate product and promoter forming compound and adding a catalyst to this solution to promote the coupling. The resulting reaction product is then purified by chromatography.

In each coupling step, the added catalyst is 1-ethyl-3-(3-dimethylaminopropyl) carbodiimide (hereinafter EDAC). This catalyst promotes coupling through amide linkages as explained in Bodansky, M. and Ondett, M.S., *Peptide Synthesis* (Interscience, New York, 1966).

DETAILED DESCRIPTION OF THE INVENTION

As indicated above, this invention relates to certain innovative and novel compounds formed from coupling an intermediate phloretin or phlorizin derivative to an undigestible and non-absorbable matrix. The resultant compounds have pharmacological efficacies (1) since the phloretin or phlorizin moiety acts as an inhibitor of sugar uptake through a mechanism involving the sugar transporter of the intestine and (2) the undigestible and non-absorbable matrix prevents the phloretin or phlorizin from entering the bloodstream and causing systemic, toxic effects throughout the body tissues.

The phloretin derivatives used as intermediates in preparing the inhibitory compounds of the present invention are substituted in the 3' C position by various primary amines. The phlorizin derivatives used as intermediates in preparing the inhibitory compounds of the present invention are substituted in the 5' C positon also with primary amines. Benzylamine is just one example of an appropriate amine that may be used for this substitution resulting in the formation of phloretin-3'-benzylamine, 4'-deoxyphlorizin-5'-benzylamine and phlorizin-5'-benzylamine.

Substitution of a primary amine in the positions indicated assures that the critical structure and geometric configuration of the phloretin and phlorizin moiety responsible for and essential to sugar transport inhibitory action are retained. Further, the free amino terminus of the primary amine provides the structure necessary for linking the inhibitor derivative to the undigestible and non-absorbable matrix via an amide linkage. The amide linkages formed are resistant to the proteolytic enzymes of the digestive tract. For example, exopeptidase enzymes require a terminal free amino acid and none are present in the resulting compound of the invention. Further, the internal amide bonds should not be cleaved by endopeptidases since critical recognition moities, such as lysine and arginine, are not present. The amide bonds are also unaffected by the mildly alkaline conditions of the small intestine. Thus, the compounds of the present invention pass through the intestine intact, thereby eliminating the toxic and systemic side effects associated with unbound phloretin and phlorizin as known in the art.

The compounds of the present invention are formed by serially coupling an undigestible and non-absorbable matrix with a leash forming compound, an active intermediate phloretin or phlorizin derivative and a promoter forming compound. The matrix is a polysaccharide having 150-500 monomeric units of glucose, mannose, and/or galactose. Appropriate functional groups are provided on the free primary hydroxyl or free secondary hydroxyls of the monomers as coupling sites. Functional groups include carboxymethyl, 2-hydroxy-3-bromopropyl, aminopropyl-diethoxysilane, amine and amide. The matrix is of a high molecular weight of at least 25,000-90,000 daltons.

Carboxymethylcellulose (CMC) is just one example of an undigestible and non-absorbable matrix bearing staple spacer arms of appropriate length so that each attached inhibiting phloretin or phlorizin moiety is held away from the polymeric backbone and free to interact with and inhibit the glucose transporter in the intestinal cell membrane. Sodium substituted carboxymethylcellulose (cellulose gum; available from Hercules, Inc.) is inexpensive and has stable $-O-CH_2CO_2H$ groupings that can easily be extended by glycine through which the inhibitor moiety may be attached. It also possesses a carbohydrate skeleton that is resistant to mammalian amylases. Further, the sodium provides improved water solubility over the unsubstituted carboxymethylcellulose. This improved solubility aids in the method of producing the compounds of the present invention as will be discussed below.

A carboxymethyl derivative of a galactomannan from the guar plant may also be used. It is a water-miscible gel having a molecular weight of about 220,000 daltons. It also is not digestible by the mammalian intestine.

A small, water soluble cross-linked dextran having a molecular weight of about 70,000 daltons may be used as a matrix material. The dextran matrix has the advantage of accessibility to the intestinal mucosa. Further, it is available from Pharmacia Fine Chemicals in a bromohydroxypropyl activated form. The bromohydroxypropyl groups react with primary amines, such as the benzylamine moiety of the intermediate inhibitor derivative to form stable secondary amine linkages, thereby avoiding the formation of peptide linkages that may be cleaved by peptidases in the gut.

CH-Sepharose could also be used as a matrix material. Advantageously, it offers a stable, hydrophobic leash for spacing the inhibitor derivative from the matrix backbone so that it is more suitably located for reaction with the sugar transporter of the brush border membrane. While one peptide bond is required in the linkage, it is formed with the aromatic amino group of an inhibitor derivative such as phlorezin-5'-benzylamine and, therefore, is highly unlikely to be cleaved by peptidases.

A further example of a matrix material is a N-hydroxysuccinimide-activated ester of a derivatized cross-linked agarose gel bead support (such as Affigel 15 available from Biorad Laboratories). Although it is insoluble, it can be used to couple an amine containing ligand, such as phlorezin-5'-benzylamine, spontaneously in aqueous solution. The matrix includes a 15-atom spacer arm containing a cationic charge that advantageously significantly enhances its interaction with the negatively charged outer sialoglyco-proteins of the mucosa. This serves to direct the inhibitor moiety toward its site of action.

A leash forming compound is coupled to the matrix material to form a first intermediate product. The molar proportions of the leash forming compound to the matrix compound should provide for 0-100% coupling of the leash forming compound to the functional groups of the matrix The leash forming compound serves to project from the backbone of the matrix and provide a site for attachment of the inhibitor moiety allowing free interaction between the inhibitor moiety and the transporter in the membrane. Glycine is the preferred leash forming compound. It provides a stable "spacer arm" for attachment of the inhibitor moiety to the matrix. The amide bonds formed between the glycine and the inhibitor derivative resist cleavage by the proteolytic enzymes of the digestive tract to retain the compound of the present invention intact. Glycine also adds "flexibility" to the inhibitor moiety. Glycine forms a variety of leash links due to the presence of dimers and trimers of glycine. Thus, some of the inhibitor moieties should always be a favorable distance from the brush border membrane to readily react with the transporter of the membrane surface. Examples of other leash forming compounds include N,N-diaminoproplymethylamine, tartaric acid, glutardialdehyde, and amino acids with the formula $NH_2-(CHOH)_n-CO_2H$, wherein $n=1-6$.

The first intermediate product resulting from the coupling of the matrix to the leash forming compound is then coupled with the intermediate phloretin or phlorizin primary amine derivative to form a second intermediate product. The coupling of the inhibitor moiety to the first intermediate product is through the amine group so as to provide an amide linkage. Coupling of the inhibitor moiety occurs at the ends of the leash forming compounds on the matrix or to the functional groups of the matrix previously uncoupled by the leash forming compound. Thus, inhibitor moieties of the compound of the present invention are located at varying distances from the matrix backbone so that some of the inhibitor moieties are always located in the ideal position for interacting with the transporter of the brush border membrane.

The compound resulting from serially coupling the leash forming compound and intermediate inhibitory compound to the matrix may itself be used for inhibiting sugar uptake in the treatment of diabetes, obesity and dumping syndrome. It should be recognized, however, that there may still remain free functional groups on the matrix such as carboxy groups that tend to make the resulting compound highly anionic at neutral pH's. Since the brush border membrane is highly negatively charged, repulsive forces may be present to prevent this compound from effectively interacting with the membrane. In order to overcome this problem, it is preferred to use the compound resulting from serially coupling the leash and inhibitor moieties to the matrix as a second intermediate product. The second intermediate product is then coupled to a promoter forming compound. The promoter forming compound couples to and covers up any remaining free carboxy groups or other functional groups on the matrix previously unreacted with the leash forming compound or the intermediate inhibitor derivative. Advantageously, the promoter forming compounds not only reduce or eliminate the polyanionic nature of the second intermediate product, but they also enhance the affinity of the resulting inhibitor compound of the present invention for the membrane surface by contributing positive charges to the compound through their free amino termini. Specific examples of promoter forming compounds include ethylenediamine and ethanolamine. Like the leash forming compounds and the intermediate inhibitor compounds coupled to the matrix, these promoter forming compounds are linked via amide linkages that are resistant to cleavage in the digestive tract.

In accordance with another aspect of the present invention, the compounds may be utilized in a method of treating diabetes. Particularly, the compounds of the present invention inhibit sugar uptake and provide control of post-prandial hyperglycemic episodes. Advantageously, the compounds of the present invention do this without toxic side effects and without inhibiting uptake of other essential nutrients.

The compounds may also safely be utilized in a method to provide weight control. By selectively inhibiting sugar uptake the compounds provide a reduction in absorbed calories without the need of harsh dietary discipline. By this, it is meant that a normal meal may be ingested but it provides fewer absorbed calories just as if food intake were reduced.

Additionally, the compounds may be utilized in a method of treating dumping syndrome. Following a gastrointestinal resection, food passes directly into the small intestine. This results in a very rapid increase of sugar absorption into the bloodstream. The pancreas then reacts by producing more insulin. The reaction time is too slow, however, and the peak insulin level occurs well after peak sugar levels. Thus, the blood glucose drops rapidly rather than leveling off as would normally occur. This results in hypoglycemia and, in severe cases, loss of consciousness. The compounds of the present invention avoid this problem by initially inhibiting absorption of the sugar. Thus, the compounds reduce or eliminate the very rapid increase of sugar absorption, thereby reducing the high insulin requirements of the individual and the degree of reaction of the pancreas. Consequently, the compounds of the present invention prevent the large fluctuation in blood glucose levels typical of dumping syndrome and that often result in loss of consciousness.

Preferably, compounds of the present invention are administered orally in tablet or capsule form. The tablets or capsules may include an enteric coating to protect the compound from the acidic environment of the stomach. The tablets and capsules may include a composition having compounds of the present invention, as the active ingredient, admixed with excipients known in the art. Thus, the tablet or capsule may contain a gum, starch, gelatin or even a buffer. The dosage for treatment with the inhibitory compounds of the present invention depends on such factors as the age, weight and condition of the individual patient as well as the condition being treated. The compound should be administered before meals if maximum effect is to be obtained.

In accordance with still another aspect of the invention methods for making the inhibitory compounds are provided. The methods include coupling a primary amine derivative of phloretin or phlorizin in accordance with one of the following formulae:

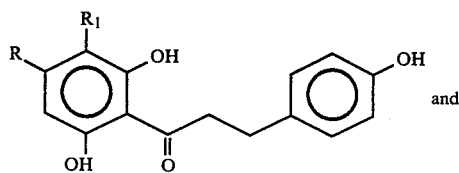
and

-continued

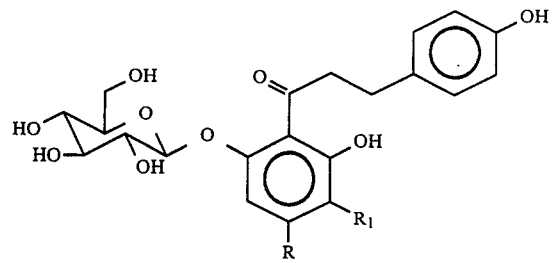

wherein R is —OH or H and $R_1$ is a primary amine moiety; to an undigestible and non-absorbable matrix.

The method includes the initial step of coupling a leash forming compound with the matrix to form a first intermediate product. The leash forming compound and matrix are preferably dissolved in water but other appropriate solvents may be used. The pH of the solutions containing the compounds is then brought to about 5.8 as, for example, by the addition of HCl as necessary. EDAC catalyst is then added to the solution to promote the coupling through amide linkages. During the coupling the solution pH is maintained at substantially 5.8. Following completion of the reaction, the solution containing the first intermediate product is purified. The purifying step is performed by dialyzing the solution against water to remove the remaining catalyst, excess starting materials and any unwanted by-products of the reaction.

The purified first intermediate product is then again dissolved in water and the intermediate inhibitory phloretin or phlorizin compound is dissolved in an appropriate solvent miscible with water, such as ethanol. The solutions containing the first intermediate product and intermediate inhibitory compound are then mixed together with the pH level brought to substantially 5.8 and the ethanol level brought to approximately 15%. EDAC catalyst is added to the mixed solutions to promote the formation of amide linkages between the intermediate inhibitory compound and the ends of the leashes and/or any unreacted functional groups of the matrix. The EDAC catalyst promoted amide linkages between the inhibitory compound and the matrix are not cleaved by the enzymes of the gastrointestinal tract and the phloretin/phlorizin moiety remains bound to the matrix. Thus, the phloretin/phlorizin moiety does not enter the bloodstream and elicit toxic effects on other organs of the body.

Following chromatographic purification, the resulting second intermediate product may be utilized in a method of treating individuals where inhibiting sugar uptake is desired. It is preferred, however, to couple the second intermediate product to a promoter forming compound so as to increase the affinity of the inhibitor product of the present invention for the mammalian brush border membrane. This is done by preparing a solution of the second intermediate product and the promoter forming compound. The pH of this solution is brought to substantially 5.8 and EDAC catalyst is added to promote the coupling.

The following examples are presented to illustrate the invention but it is not to be considered as limited thereto.

EXAMPLE 1

Phlorizin (7 mmol) and p-nitrobenzaldehyde (5 mmol) were dissolved in 84 ml methanol and cooled to 0° C. Under a nitrogen atmosphere, 14 meq of 1 N KOH were added dropwise with magnetic stirring and the reaction was allowed to incubate for 2 hr at 0° C. and then 1.5 hr at 50° C. The reaction mixture was recooled to 0° C. and neutralized by the dropwise addition of 14 meq of 0.5 N HCl. The solvent was removed in vacuo to yield a brown syrup containing primarily the presumed carbinol (carbinol was not sufficiently stable to be analyzed) and unreacted phlorizin. The mixture was dissolved in 10 ml CHCl$_3$/CH$_3$OH (4:1) and subjected to flash chromatography on a column of Silica Gel 60 (4.5×26 cm) that had been pressure packed with chloroform. Elution was conducted with 0.75 L 15% methanol in chloroform, followed by 0.5 L 18% and then 0.5 L 22% of the same solvent mixture. Thin layer chromatography was used to monitor the fractionation: the eluate volume between 0.4–0.5 L contained essentially pure 2'-O-β-D-glucopyranosyl)-5'-p-nitrobenzyl carbinol (herinafter called GNC) (0.8 g, 20%) while the 0.5–1.4 L eluate contained 2.4 g of a mixture of GNC contaminated with approximately 20% phlorizin. R$_f$ value of the presumed carbinol GNC in 25% MeOH/CHCl$_3$ was 0.25.

Compound GNC (0.96 g in 100 ml methanol) was catalytically hydrogenated with 150 mg 10% Pd on charcoal for 1 hr at 22° C. at atmospheric pressure, and then 3 hr at 55° C. at 30 cm H$_2$O pressure. At lower temperatures reduction was incomplete and yielded an unstable orange product. The catalyst was removed and the methanol was evaporated in vacuo to yield crude phlorizin-5'-benzylamine (0.84 g, 92%) The product was dissolved in 8 ml methanol and mixed with 10 ml Sephadex G-10 slurry equilibrated in 50% methanol. Finally 8 ml H$_2$O was added and the resulting slurry was added to the top of a Sephadex G-10 column (2.5×27 cm) likewise equilibrated in 50% methanol. Elution was conducted with 0.8 L 50% methanol followed by 0.7 L 55% methanol and 1.0 L 60% methanol. The amine was eluted in the 1.1–2.0 L fraction. If the amine had been contaminated prior to this chromatography, phlorizin was readily separated at this step and could be recovered in the 0.36–0.66 L fraction. Phlorizin-5'-benzylamine was obtained by evaporating the solvent and crystallization from aqueous methanol as the monohydrate (0.55 g, 60%); after drying at 80° C. in vacuo its m.p. was 197°–200° C.

| Elemental Analysis: | C | H | N |
|---|---|---|---|
| Calculated for C$_{28}$H$_{31}$O$_{10}$N.H$_2$O: | 60.10 | 5.94 | 2.54 |
| Found for the reaction product: | 60.30 | 5.90 | 2.51 |

In order to verify that the reaction conditions were sufficient to reduce the secondary hydroxyl group of GNC, the phlorizin-5'-benzylamine reaction product was quantitatively acetylated with acetic anhydride in the presence of pyridine. Theoretical incorporation is 8 moles acetate/mole glycoside. Found for phlorizin-5'-benzylamine: 7.82 moles acetate/mole phlorizin-5'-benzylamine (97.8%).

An acetamide derivative of the reaction product prepared by coupling acetic acid and the amine in methanol with EDAC, was crystallized from 30% methanol as the monohydrate. After drying at 80° C. in vacuo its m.p. was: 215° C. after softening at 149° C.

| Elemental Analysis: | C | H | N |
|---|---|---|---|
| Calculated for C$_{30}$H$_{33}$O$_{11}$N: | 61.64 | 5.69 | 2.49 |
| Found for acetamide derivative of the reaction product: | 61.58 | 5.90 | 2.32 |

The structure proposed for compound phlorizin-5'-benzylamine was confirmed by comparing its proton NMR spectra with that of phlorizin. The A$_2$B$_2$ pattern at 2.88 and 3.50 ppm arising from the —CH$_2$CH$_2$CO— moiety in phlorizin also appears at 2.87 and 3.49 ppm in the spectra of phlorizin-5'-benzylamine (in both compounds the triplet at 3.5 ppm is partially obscured by the signals arising from the protons in the glucose moiety). The B-ring AA'BB'-system at 6.72 and 7.10 ppm remained unchanged, but phlorizin's A-ring AB-system at 5.99 and 6.25 ppm was converted to a 1 H singlet at 7.42 ppm in compound phlorizin-5'-benzylamine. The new C ring AA'BB' system in compound phlorizin-5'benzylamine gave signals at 6.54 and 6.98 ppm and the new —CH$_2$ group is seen as a 2H singlet at 3.72 ppm. The reaction is schematically shown below.

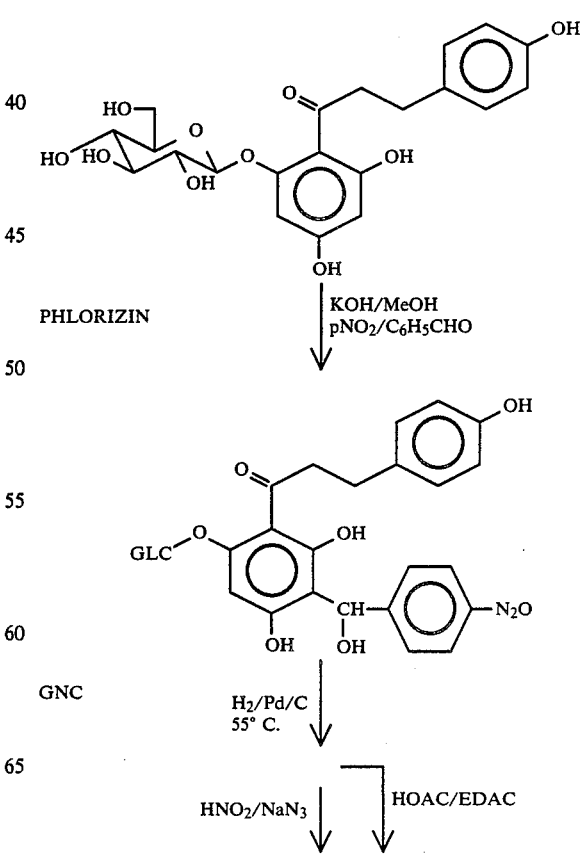

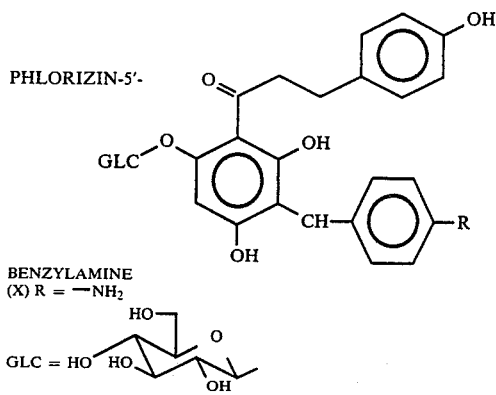

PHLORIZIN-5'-
BENZYLAMINE
(X) R = —NH₂

This example demonstrates the synthesis of an intermediate phlorizin derivative having a primary amine moiety on the 5'C. The synthesis of an intermediate phloretin derivative having an primary amine moiety on the 3'C is set forth in "Phloretinyl-3'-benzylazide: A-High Affinity, Probe for the Sugar Transporter in Human Erythrocytes", Fannin, F. F., Evans, J. O., Gibbs, E. M., Deidrich, D. F., Biochemica et Biophysica Acta, 649 (1981) 189–201.

EXAMPLE 2

Sodium carboxymethylcellulose (CMC) (0.0625 gm; 0.213 mmoles of —$CO_2H$ groups i.e. 70% of anhydroglucose units carry carboxymethyl groups) was dissolved in 9 ml of water. To this solution was added 1 ml aqueous solution of 80 mg radioactive glycine (1.066 mmoles; 1.2$\mu$Ci$^{14}$C). The solution was made to a pH of 5.8 with 0.2 N HCl. Then 123 mg of solid EDAC was added with stirring. As successful coupling reactions consumed hydrogen ions, the pH was maintained at 5.8 by the addition of 0.2 N HCl as required.

The resultant reaction mixture was then dialyzed against 1 liter of water for 7 hours using a Spectrapor dialysis membrane (MW cutoff 6,000–8,000 daltons). This was done as it is important to remove excess starting materials, by-products and spent catalyst from the first reaction in order to perform the next coupling step in the overall synthesis set forth in Example 3 below.

A number of other test reactions were performed to ascertain the optimal reaction conditions that yield the greatest coupling of CMC and glycine.

TABLE 1

| MOLAR RATIOS OF | | | EXTENT OF REACTION: mMoles of Glycine coupled to CMC carboxyl groups / total mMoles of available, reactive carboxyl groups |
|---|---|---|---|
| CMC—COOH'S | Glycine | EDAC catalyst | |
| Rxn I-pH 5.8 1:5:3 | | | 82% |
| Rxn II-pH 5.8 1:10:3 | | | 87% |
| Rxn III-pH 6.8 1:5:3 | | | 35% |
| Rxn IV-pH 6.8 1:10:3 | | | 55% |
| Rxn V-pH 4.8 1:1000:100 | | | 0% |
| Rxn VI-pH 6 1:1000:100 | | | 0% |

The pH of the reaction as well as the molar ratios of the materials (CMC-matrix carboxyl groups: glycine ligand; EDAC catalyst) were varied. The % yield of glycinated cellulose was assessed by Sephadex gel filtration. Specifically, the radioactive glycinated-cellulose product (first intermediate product of the overall synthesis) was separated from excess starting materials, by-products and catalyst using a Sephadex G-25 column. Void volumes (determined with Blue Dextran) and approximate column volumes were 11 ml and 22 ml, respectively. Aliquots of reactions I-VI from Table 1 were applied and eluted with water. Then one ml fractions were collected and assayed for $^{14}$C.

As shown in FIG. 1, the small Sephadex column readily separated the 90,000 dalton glycinated-cellulose product from the low molecular weight unreacted glycine and other products (dimers and trimers, etc. of glycine) that enter the beads and were eluted only after a column volume of water. The results of these tests, summarized in Table 1, indicate that:

(1) high molar ratios of glycine and EDAC catalyst relative to the equivalents of available CMC-carboxyl groups prevent coupling (see reactions V and VI); apparently the excess glycine —$CO_2H$'s compete with those on the CMC such that only glycylglycine and higher oligomers are formed; and (2) the lower pH of 5.8 improves yield and when molar ratios of CMC—$CO_2H$: glycine: catalyst are 1:10:3, over 80% coupling occurs.

EXAMPLE 3

To the dialyzed first intermediate product of Example 2 was added 190 mg of radioactive phlorizin-5-benzylamine (0.35 mmoles; 100$\mu$Ci$^3$H) in ethanol from Example 1. Solid EDAC catalyst (100 mg; 0.52 mmoles) was then added to the solution and the reaction was allowed to proceed for six hours. During this time the ethanol level of the solution was maintained at 15%, the temperature of the solution at 35°–40° C. and the pH was maintained at 5.8. The reaction yielded a white product (CMC-glycine-phlorizin-5'-benzylamine) as a suspension with 20% of the —$CO_2H$ groups coupled with the amine derivative of phlorizin.

To 6.5 ml of the suspension was added 150$\mu$L of 0.5 N NaOH to dissolve the product. This solution was then chromatographed on a Sephadex G-25 column (void volume 180–190 ml; hold up volume, 275 ml) with water as eluant. The second intermediate product, CMC-glycine-phlorizin-5'-benzylamine, was eluted in 25 ml at about the void volume. The second intermediate product was completely separated from unreacted $^3$H-phlorizon-5'-benzylamine because that starting material is tightly absorbed to the Sephadex G-25 and requires ethanol to be eluted.

Aliquots of the fractionated reaction product were used to determine the extent of binding between the CMC—[$^{14}$C] glycine and the [$^3$H] phlorizin-5'-benzylamine. The amount of CMC-reactive groups recovered in the water elution (92%, as determined from the [$^{14}$C] CPM applied) was compared to the phlorizin-5'-benzylamine present in these same fractions (as measured by the bound [$^3$H] CPM).

Aliquots of the Sephadex G-25 purified second intermediate product were also examined with a TNBS assay (see Antoni, G., Presentini, R. and Neri, P., Anal. Biochem. 129 (1983) 6063). The reagent 2,4,6-trinitrobenzene sulfonic acid forms a yellow color with free primary amine groups that is measured spectrophotometrically. The results of the analysis indicate that the G-25 purified product contained only trace amounts of free amino groups. Therefore, from 87-100% of the phlorizin-5'-benzylamine is coupled to the matrix through the amino group. Had the ligand been coupled in reverse fashion as, for example, through its phenol groups, free amino groups could have been detected.

An awareness of the mode of coupling is crucial since phlorizin possesses sugar transport inhibitory properties only when the phenolic groups are free to react with the cell membrane surface. Thus, the phlorizin moieties bound to the cellulose matrix in this preparation are in optimal configuration for interaction with the intestinal sugar transport system.

Further experimentation has shown that the preferred molar ratio of glycinated CMC to phlorizin-5'-benzylamine to EDAC catalyst is 1:0.2:0.75. While larger amounts of phlorizin-5'-benzylamine may be readily incorporated into the product, such incorporation results in a loss of water solubility. The loss of water solubility is to be avoided as it adversely effects the efficiency of the following reaction step and the pharmacological activity of the completed compound.

EXAMPLE 4

To a 9 ml aliquot of the eluted solution of Example 3 containing the second intermediate product (CMC-glycine-phlorizin-5'-benzylamine) (containing approximately 2 mmoles of underivatized —$CO_2H$ groups) was added 125 µL of a solution containing 10.6 mmoles of ethanolamine hydrochloride. The pH of the solution was brought to 5.8 and 2 mg. of solid EDAC catalyst was added. The addition of the catalyst resulted in a rapid increase in pH signifying the coupling of the amine to the matrix. Within 1 hour the pH decreased to about 5 signifying near completion of the reaction. The mixture was then maintained at 4 C overnight. The final product was purified by chromatography on a Sephadex G-25 column. Eighty-eight percent of the radiolabeled product was recovered and it possessed the expected $^{14}C/^{3}H$ ratio of 0.018.

EXAMPLE 5

An animal study was then conducted to determine whether bacterial and other digestive action would split the inhibitory compound of the present invention, thereby leading to the absorption of toxic fragments. The radioactive labeled compound of Example 4 (0.3 /µ Ci $^{3}H$ labeled phlorizin moiety; 0.04µCi$^{14}C$ labeled CMC) was inserted into the bowels of a single rat that possessed a cecal fistula. No radioactivity was found in the blood plasma one or six hours after administration. Furthermore, the radioactive material recovered from the bowel contents contained a $^{3}H/^{14}C$ ratio equal to that of the original material. Thus, fragmentation and selective absorption or disposal of either labeled fragment did not occur.

In summary, numerous benefits have been described which result from employing the concepts of the present invention. A novel intermediate compound having potential pharmacological efficacies is disclosed. Compounds having selective sugar transport inhibitory action are also disclosed. These compounds include an amino derivative of phloretin or phlorizin bound through an amide linkage to an undigestible and non-absorbable matrix. Thus, the compounds avoid the known systemic effects of phlorizin and phloretin while advantageously providing their specific inhibitory action. Further methods for utilizing the chemically safe compounds in treating diabetics, the obese and gastrointestinal resection patients are disclosed.

The invention has been described herein with reference to certain preferred embodiments. However, as obvious variations thereon will become apparent to those skilled in the art, the invention is not to be considered as limited thereto.

We claim:

1. A compound, consisting of: a reaction product formed by serially coupling (1) an undigestible and non-absorbable polysaccharide matrix with a leash forming compound selected from a group consisting of glycine, N-N-diaminopropylmethylamine, tartaric acid, glutardialdehyde and $NH_2$—$(CHOH)_n$—$CO_2H$ wherein n=1-6 by dissolving the leash forming compound and matrix together in a solvent maintained at a pH of substantially 5.8 and then adding 1-ethyl-3-(3-dimethylaminopropyl) carbodiimide HCl as a catalyst to promote coupling and obtain a first intermediate product; (2) said first intermediate product with an intermediate inhibitory compound selected from a group consisting of compounds having the following structures:

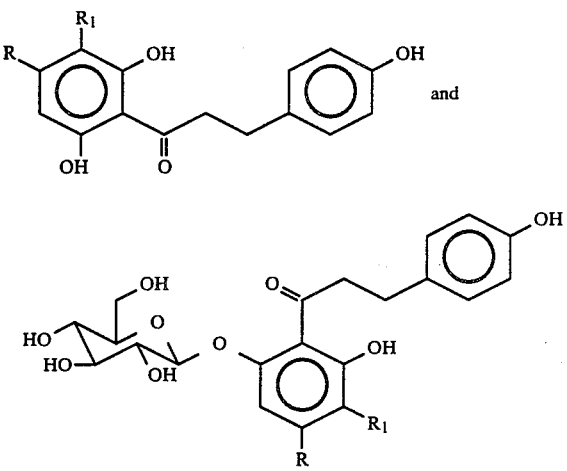

wherein R=—OH or —H and $R_1$ is a primary amine of from 1-10 carbon atoms effective in inhibiting glucose uptake by dissolving said first intermediate product and said intermediate inhibitory compound in solvents, mixing the solvents, and adding 1-ethyl-3-(3-dimethylaminopropyl) carbodiimide HCl as a catalyst to promote coupling while maintaining the pH of the mixed solvents at substantially 5.8 so as to form a second intermediate product; and (3) said second intermediate product with a promoter forming compound selected from a group consisting of ethylenediamine and ethanolamine by dissolving said promoter forming compound and said second intermediate product in solvent maintained at a pH of substantially 5.8 and adding 1-ethyl-3-(3-dimethylaminopropyl) carbodiimide HCl as a catalyst.

2. The compound of claim 1, wherein $R_1$ includes an aromatic ring.

3. The compound of claim 1, wherein said intermediate inhibitory compound is phlorizin-5'-benzylamine.

4. The compound of claim 1, wherein said intermediate inhibitory compound is 4'-deoxyphlorizin-5'-benzylamine.

5. The compound of claim 1, wherein said intermediate inhibitory compound is phloretin-3'-benzylamine.

6. The compound of claim 1, wherein said polysaccharide matrix has a molecular weight of from 25,000-90,000 daltons.

7. The compound of claim 1, wherein said polysaccharide matrix includes substantially 150-500 monomeric units selected from a group consisting of

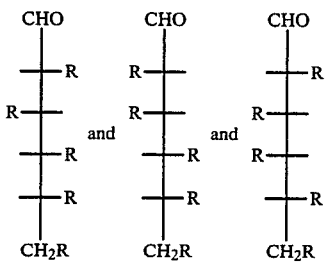

and any mixtures thereof, wherein R=—OH, —O—CH₂—CO₂H, —O—CH₂—CHOH—CH₂Br, —Si(OC₂H₅)₂—C₃H₆NH₂, —NH₂, or —NH—CO—CH₃.

8. The compound of claim 1, wherein said matrix is carboxymethylcellulose.

9. The compound of claim 1, wherein said matrix is sodium carboxymethylcellulose.

10. The compound of claim 1, wherein said matrix is a carboxymethyl derivative of a galactomannan from the guar plant.

11. The compound of claim 1, wherein said matrix is a water soluble cross-linked dextran of substantially 70,000 daltons.

12. The compound of claim 1, wherein said matrix is CH-Sepharose.

13. The compound of claim 1, wherein said matrix is an N-hydroxysuccinimide-activated ester of a derivatized cross-linked agarose gel bead support.

14. A compound effective in inhibiting glucose uptake in a mammalian intestine, consisting of: a reaction product formed by serially coupling (1) a polysaccharide matrix with a leash forming compound selected from a group consisting of glycine, N-N-diaminopropylmethylamine, tartaric acid, glutardialdehyde and NH₂—(CHOH)ₙ—CO₂H wherein n=1-6 by dissolving the leash forming compound and matrix together in a solvent maintained at a pH of substantially 5.8 and then adding 1-ethyl-3-(3-dimethylaminopropyl) carbodiimide HCl as a catalyst to promote coupling and obtain a first intermediate product and (2) said first intermediate product with an intermediate inhibitory compound selected from a group consisting of compounds having the following structures:

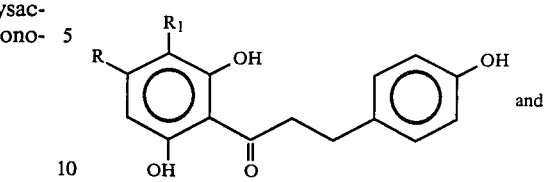

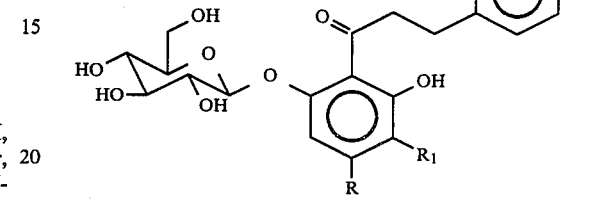

wherein R=—OH or —H and R₁ is a primary amine of from 1-10 carbon atoms by dissolving said first intermediate product and said intermediate inhibitory compound in solvents, mixing the solvents, and adding 1-ethyl-3-(3-dimethylaminopropyl) carboddimide HCl as a catalyst to promote coupling while maintaining the pH of the mixed solvents at substantially 5.8.

15. The compound of claim 14, wherein said polysaccharide matrix includes monomeric units selected from a group consisting of

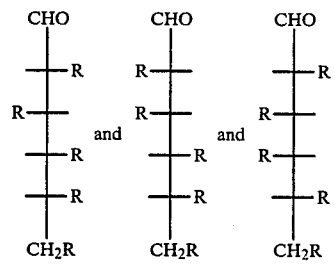

and any mixtures thereof, wherein R=—OH, —O—CH₂—CO₂—CO₂H, —O—CH₂—CHOH—CH₂Br, —Si(OC₂H₅)₂—C₃H₆NH₂; —NH₂, or —NH—CO—CH₃.

* * * * *